(12) United States Patent
Werner et al.

(10) Patent No.: US 9,752,969 B2
(45) Date of Patent: Sep. 5, 2017

(54) UNIVERSAL MECHANICAL TESTER FOR MEASURING FRICTION AND WEAR CHARACTERISTICS OF MATERIALS

(71) Applicants: Douglas Werner, Campbell, CA (US); Vladislov Dorfman, Campbell, CA (US); Adrian Correa, Campbell, CA (US); William Sloan, Campbell, CA (US)

(72) Inventors: Douglas Werner, Campbell, CA (US); Vladislov Dorfman, Campbell, CA (US); Adrian Correa, Campbell, CA (US); William Sloan, Campbell, CA (US)

(73) Assignee: BRUKER NANO INC., Santa Barbara, CA (US)

(*) Notice: Subject to any disclaimer, the term of this patent is extended or adjusted under 35 U.S.C. 154(b) by 217 days.

(21) Appl. No.: 14/682,115

(22) Filed: Apr. 9, 2015

(65) Prior Publication Data

US 2015/0293001 A1 Oct. 15, 2015

Related U.S. Application Data

(60) Provisional application No. 61/977,457, filed on Apr. 9, 2014.

(51) Int. Cl.
*G01N 3/56* (2006.01)
*G01K 13/00* (2006.01)
*G01N 29/04* (2006.01)
*G01N 19/02* (2006.01)
*G01N 29/14* (2006.01)

(52) U.S. Cl.
CPC ............... *G01N 3/56* (2013.01); *G01K 13/00* (2013.01); *G01N 19/02* (2013.01); *G01N 29/04* (2013.01); *G01N 29/14* (2013.01)

(58) Field of Classification Search
CPC .......... G01N 3/56; G01N 19/02; G01N 29/04; G01N 27/04; G01K 13/00
See application file for complete search history.

(56) References Cited

U.S. PATENT DOCUMENTS 5,795,990 A * 8/1998 Gitis ........................ G01N 3/56
73/10
6,418,776 B1 * 7/2002 Gitis ........................ G01N 3/56
73/10

(Continued)

*Primary Examiner* — Paul West
*Assistant Examiner* — Xin Zhong
(74) *Attorney, Agent, or Firm* — Antonio R. Durando (57) ABSTRACT

A universal tester includes modular sample stages, each dedicated to a test configuration. The modules are manually coupled to the base of the tester and automatically recognized for activation of the correct software relevant to its configuration and test scripts. As a result, no extraneous script can be activated erroneously by an operator. A single motor in the frame of the tester actuates the drive of each sample stage through a drivetrain that is automatically engaged by the manual installation of the stage. Means for controlling and/or measuring temperature, humidity, voltage, resistance, and acoustic emissions are provided through dedicated expansion slots and cards that activate respective software. An electronic identification in each card ensures that only relevant software is enabled.

17 Claims, 10 Drawing Sheets (56) References Cited

U.S. PATENT DOCUMENTS

2009/0320555 A1* 12/2009 Ebrecht .................. G01N 19/02
  73/9
2010/0122567 A1* 5/2010 Linares .................... G01N 3/56
  73/7

* cited by examiner

UNIVERSAL MECHANICAL TESTER FOR MEASURING FRICTION AND WEAR CHARACTERISTICS OF MATERIALS

RELATED APPLICATIONS

This application is based on and claims the priority of Provisional Application Ser. No. 61/977,457, filed Apr. 9, 2014.

BACKGROUND OF THE INVENTION

Field of the Invention

The invention relates in general to the field of tribology.

Description of the Prior Art

The field of tribology involves the study of friction and wear on materials. Two or more objects are brought into contact with each other and a relative motion is started between the two contacting materials for the purpose of measuring the resulting friction forces. Over time a "wear" track may be created as result of damage caused by the two materials rubbing against each other; therefore, the wear on one or both of the objects can also be measured.

There are many different configurations of mechanical testers, each performing a specific dedicated test. The present invention describes a unique piece of equipment that allows the user to perform multiple tests with multiple configurations with a single mechanical tester and interchangeable, modular sample stages and accessories.

The conventional equipment used for measuring friction and wear is dedicated to a particular test type and a corresponding test configuration. Examples include, without limitation, the configurations referred to in the art as block-on-ring, pin/ball/disk-on-disk, and reciprocating pin/ball on flat. The first represents a configuration where the sample stage includes a horizontal drive shaft rotating around its main axis. A ring specimen is coupled to the shaft for concurrent rotation and a test block is pushed radially against the edge of the ring with a known force. The friction force and/or the torque imparted on the shaft are measured, from which the coefficient of friction between the block and the specimen material can be calculated based on the known load (i.e., the normal force applied by the block).

Similarly, for the ball-on-disk, pin-on-disk or disk-on-disk test configurations, a disk specimen is mounted horizontally on a vertical rotating shaft in the sample stage. A ball or pin specimen is brought down from above into contact with the spinning face of the disk at a known radial distance from the axis of the shaft and a known normal force is applied. Thus, the frictional force between the ball or pin and the spinning disk and the resulting wear can be measured. Alternatively, a fixed disk, rather than a ball or pin, is aligned axially with the spinning disk coupled to the stage and the two are brought into contact with a known force. In this configuration the friction and wear between the two disks can similarly be measured.

The third exemplary type of test equipment is a reciprocating-type tester. In this configuration an eccentric crank arm is used to transfer the rotary motion of a vertical drive shaft to a reciprocating motion in a horizontal plane of the stage where the sample is mounted. By applying a constant rotational motion to the drive shaft, the horizontal reciprocating motion follows a sinusoidal velocity profile. A test specimen (a flat sample) is mounted on the reciprocating plane and again a ball or pin specimen is brought into contact with a known normal force. The resulting frictional force is measured and the coefficient can be calculated. Wear tests can be similarly carried out in conventional manner.

Each of these tests is normally carried out on a different, dedicated test machine. Therefore, multiple machines are required, which can be inefficient and therefore undesirable if all available machines are not used simultaneously. The capability of carrying out multiple testing requires a lot of laboratory space, which is typically the most expensive space in a production setting. It is also inefficient and expensive due to the fact that many of the same components, such as computers, controllers and sensors, are necessarily provided as duplicates for each dedicated testing unit.

U.S. Pat. No. 6,418,776 describes a universal tester wherein alternative modules, each containing a motor and a dedicated drive, are available for use in different test configurations, such as described above. Each module includes a self-contained drive with a motor and is attached to a base plate in the frame of the unit. While this type of system requires less laboratory space and can be more economical than multiple dedicated testers, each replaceable stage unit still has its own motor, which is often the single most expensive component of the replaceable module. Also, because the motor is included in each modular stage, each module is necessarily larger than desirable in relation to the space available inside the base of the instrument and therefore only relatively small motors can be used. In addition, the presence of these motors in the stage module limits the access to the sample area because of the space occupied by them and by the cables needed to supply power to the motor, all of which limits the space available for specimens attached to the carriage of the tester and for specimens mounted on the modular stage.

A universal tester of this type is also difficult for the user to configure and use properly with the software. In what has turned out to be a major problem and concern in the industry, the software must be set-up manually for each test configuration or there must be a dedicated piece of software for each test type, which can be cumbersome for the user and lead to serious mistakes when a test is not properly set up. The wrong choice of test parameters will produce misleading results; more importantly, however, it can also create dangerous situations due to unwarranted mechanical stresses that can result from erroneous test programming. If different test programs (referred to in the art as "scripts") are provided by the developer for each machine, they also require continuous technical support, which adds cost for the user as well as the supplier. This invention is directed at solving these problems with a mechanical tester capable of performing measurements in all above-described configurations with a single rotary drive.

SUMMARY OF THE INVENTION

The invention is a universal mechanical friction and wear test instrument that allows the performance of multiple test protocols with a single machine. Such result is achieved by the use of modular sample stages that do not include a motor, each dedicated to a test configuration. The modules are manually coupled to the base of the instrument and are automatically recognized for activation of the correct software relevant to its configuration and test protocols (scripts). As a result, no extraneous protocol can be activated erroneously by an operator. A single motor housed in the frame of the instrument actuates the drive of each sample stage through a drivetrain and a coupling mechanism that is automatically engaged by the manual installation of the stage.

Means for controlling and/or measuring the temperature and the humidity of the samples are provided through a bank of dedicated expansion slots, such as peripheral component interconnect (PCI) slots, available for activation of respective software by inserting corresponding expansion cards. Additional slots and respective software are also available for voltage/resistance measurements and for acoustic-emission measurements on the materials under test. An electronic identification in each card ensures that only relevant software is enabled, thereby avoiding s erroneous script implementations.

Various other advantages will become clear from the description of the invention in the specification that follows and from the novel features particularly pointed out in the appended claims. Therefore, this invention includes the features hereinafter illustrated in the drawings, fully described in the detailed description of the preferred embodiments and particularly pointed out in the claims, but such drawings and description disclose only some of the various ways in which the invention may be practiced.

DESCRIPTION OF THE PREFERRED EMBODIMENT

As used herein, the terms "specimen" and "sample" are used interchangeably to refer to the materials tested to determine their wear and friction characteristics. The term "lower" specimen (or sample) is used to refer to the material coupled to the lower holder in the modular stages of the instrument of the invention. The term "upper" specimen (or sample) is used to refer to the material coupled to the upper holder that is rigidly attached to the sensor unit in the carriage of the instrument to contact and exert a force against the lower specimen and to sense and measure the frictional reaction when a relative displacement is initiated or produced by the motion in the sample stage. As described above, the upper specimens may be a pin, a ball, a block or a disk acting on the lower specimen and the sample motion may be rotational over a horizontal axis, rotational over a vertical axis, or reciprocating linearly along a horizontal direction.

The universal mechanical tester of the invention was developed to overcome the shortcomings of the instrument described in U.S. Pat. No. 6,418,776. The improvements lie in the configuration of the modules in relation to the base and frame of the instrument and in the mechanisms used to ensure the correct and safe coupling of the module for the desired test procedure. Accordingly, the tester of the invention is not described in detail herein other than as necessary to disclose the elements of the invention. The details of the conventional portions of the instrument can be found, for example, in the description of the instrument disclosed in U.S. Pat. No. 6,418,776, which for that purpose is herein incorporated by reference in its entirety.

According to one aspect of the invention, the tester is a machine capable of accepting modular sample stages that automatically activate only test protocols appropriate for the particular module installed in the instrument. According to another aspect, a single motor is placed in the frame of the tester for driving all modular stages. Because the motor is housed in the frame, its size is not limited by space availability and it is provided so as to meet the largest power requirements intended for the instrument. In addition, the absence of a motor in the stages makes it possible to greatly reduce their size and correspondingly increase the space available for receiving test specimens in the instrument.

Figure 1:
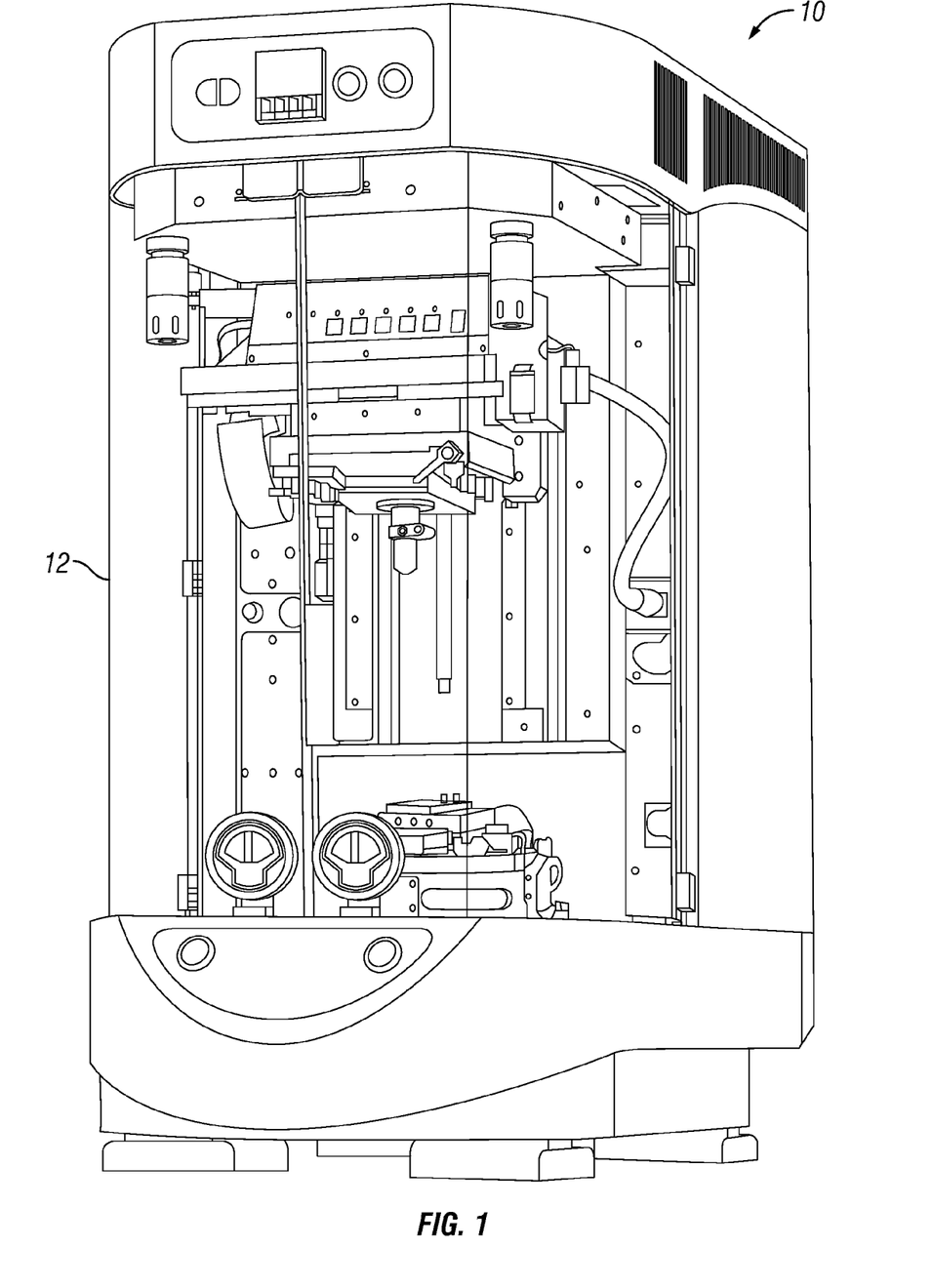
FIG. 1 is a perspective front view of a test instrument according to the invention, including a modular sample stage visible through a transparent front cover.
Figure 2:
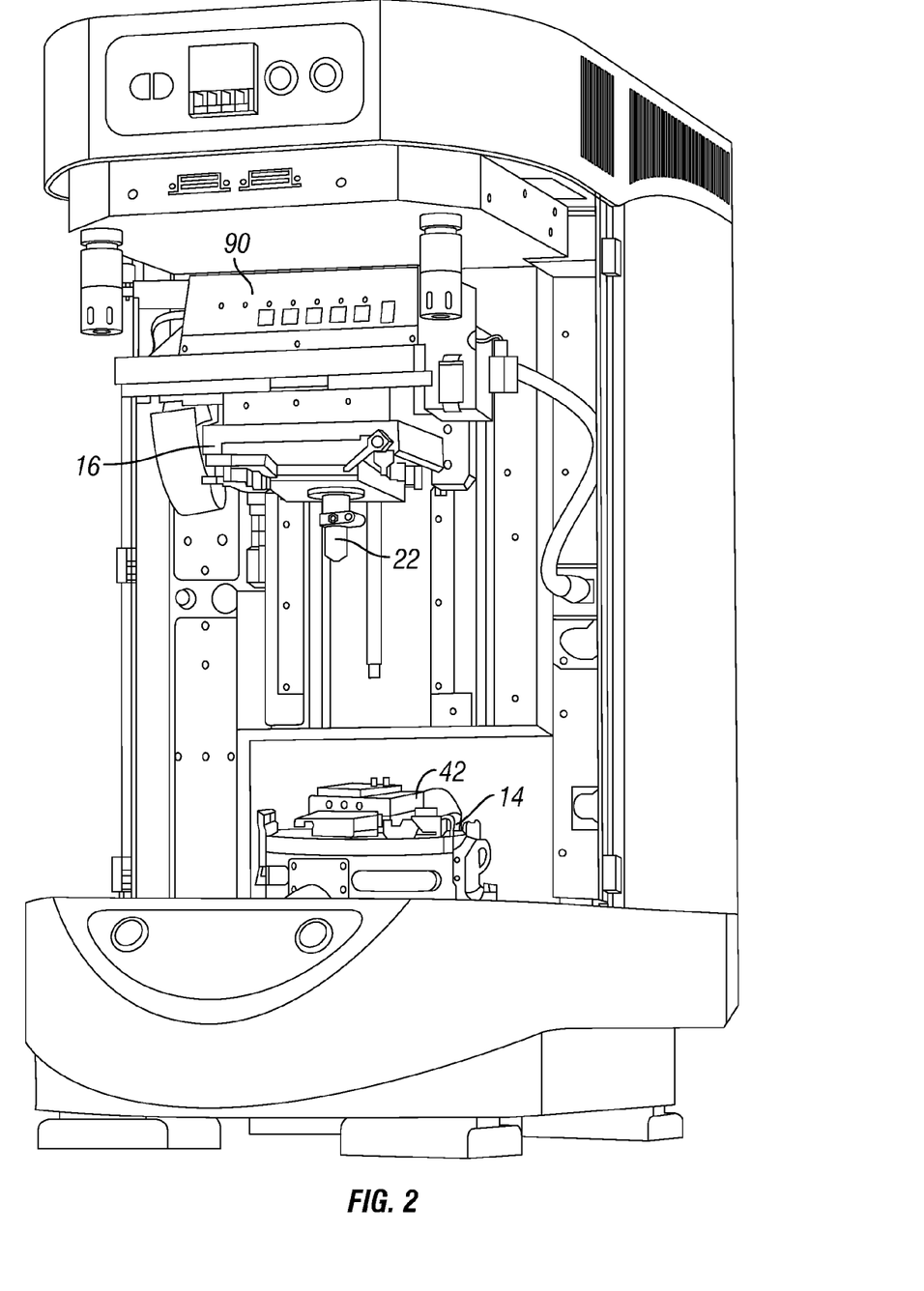
FIG. 2 is the perspective view of FIG. 1 after removal of the front cover.
Figure 3:
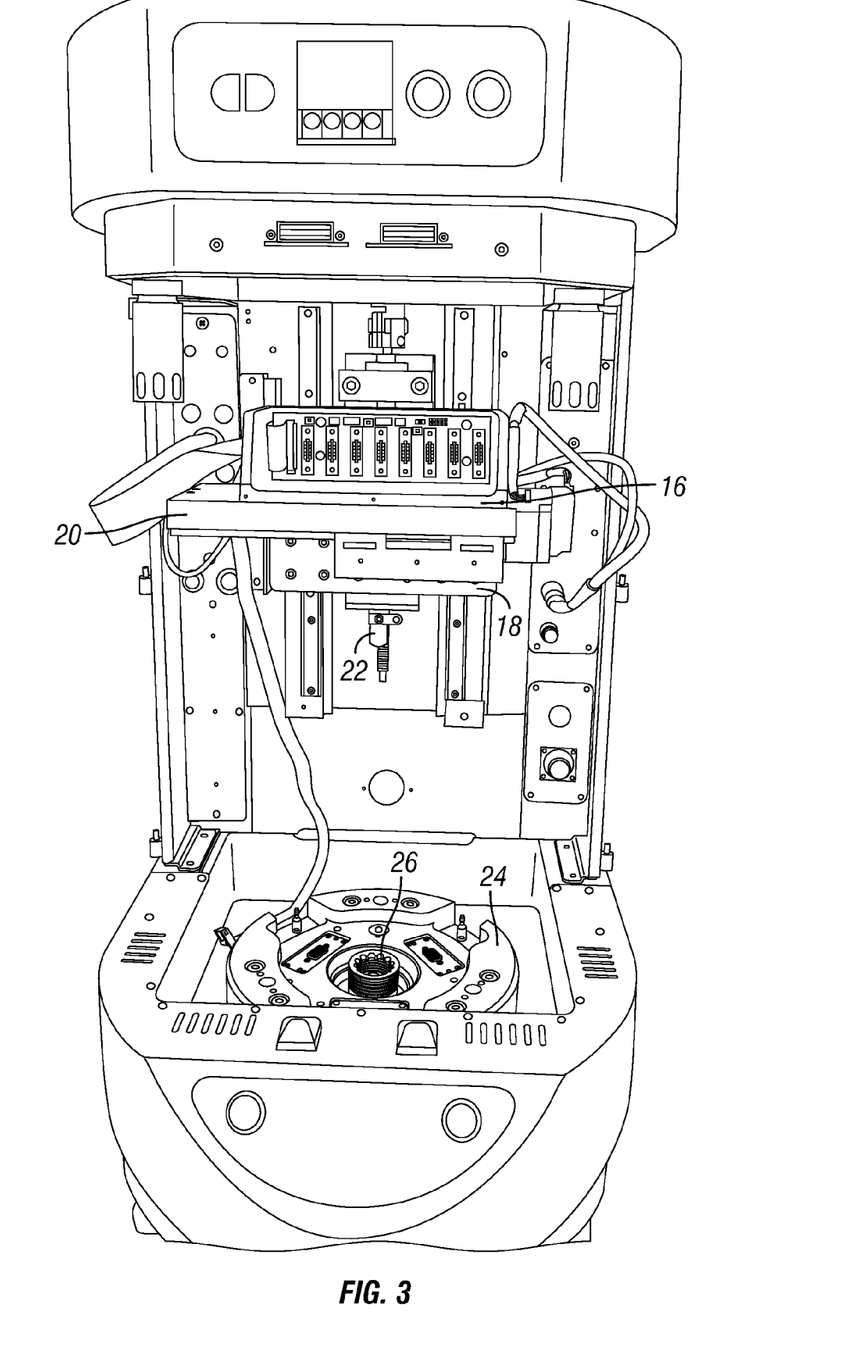
FIG. 3 is a front elevational view of the instrument of FIG. 2 after removal of the modular sample stage of the invention.

Referring to the figures, wherein like parts are designated with like numerals and symbols, FIG. 1 illustrates a tester 10 according to the invention. A transparent cover 12 encloses the test area for protection and environmental isolation of the specimens during testing, such as required for temperature and humidity control, for example. FIG. 2 shows the tester 10 without the cover 12 to illustrate the relatively large test space allowed by a modular sample stage 14 modified according to the invention. FIG. 3 shows the tester with the sample stage 14 removed from it. The vertically translatable carriage 16, the horizontally translatable slide 18, the bidirectional force sensor assembly 20, and the various related actuating mechanisms are conventional and therefore not described in detail herein. The upper holder 22 (a chuck or equivalent device) for engaging the upper specimen (pin ball, block or disk, not shown) is similarly conventional, such as described in U.S. Pat. No. 6,418,776.

Figure 4:
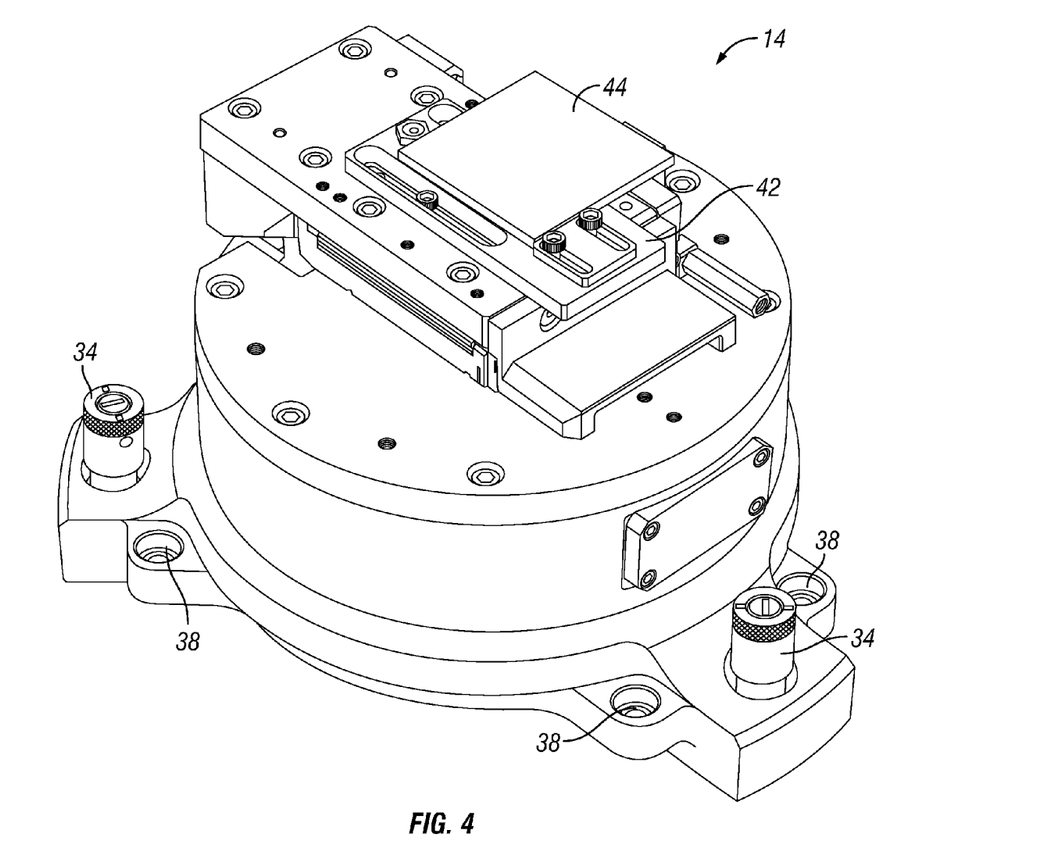
FIG. 4 is a perspective view of a modular sample stage adapted for reciprocating pin/ball on flat measurements.

As also seen in isolation in the perspective view of FIG. 4, the exemplary modular sample stage 14 is provided according to the invention for engagement within the base 24 of the tester 10. A single motor (not shown) housed in the frame of the tester is used to actuate the motion of each sample stage (for reciprocation, vertical rotation, or horizontal rotation) though a drivetrain that includes a vertical shaft protruding upward with a coupling mechanism 26 from the center of the base 24 of the tester. Such coupling mechanism is preferably a bellows-type coupling to ensure the smooth engagement of the drive shaft 28 protruding from the underside of the stage 14, as seen in the bottom view of the stage in FIG. 5. As clearly visible from the isolated view of the base 24 in FIG. 6, the shaft 28 in the stage is adapted for automatic engagement of the coupling mechanism 26 when the stage is lowered over the base 24 of the tester. Guide pins 30 in the bottom of the stage module (FIG. 5) and corresponding openings 32 in the base 24 of the instrument are provided to align the stage with the frame and secure it safely in place by means of a quick-connect locking mechanism, such as a ball lock 34 adapted to engage corresponding lock pins 36 protruding upward from the base 24. In view of the potentially large frictional forces exerted by the upper specimen on the sample tied to the stage, the stage 14 is also preferably bolted to the base 24 for additional security using dedicated openings 38,40 in the stage and base, respectively.

Figure 5:
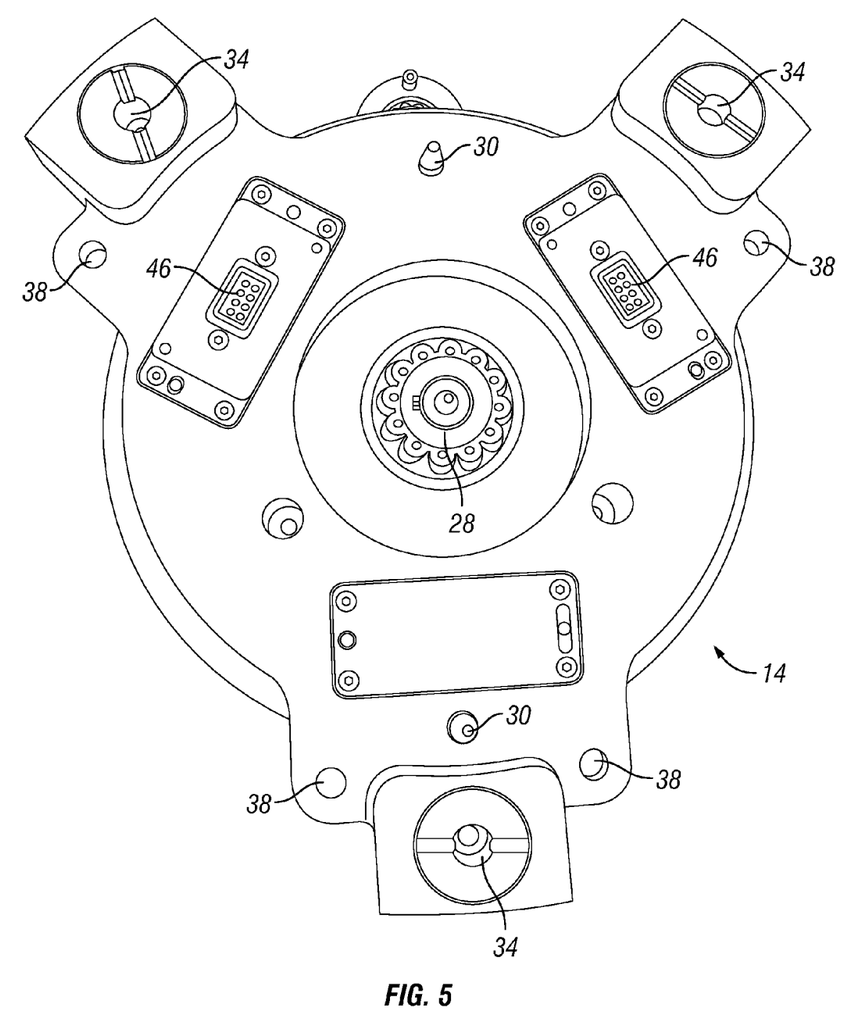
FIG. 5 is a bottom view of the modular stage of FIG. 4.
Figure 6:
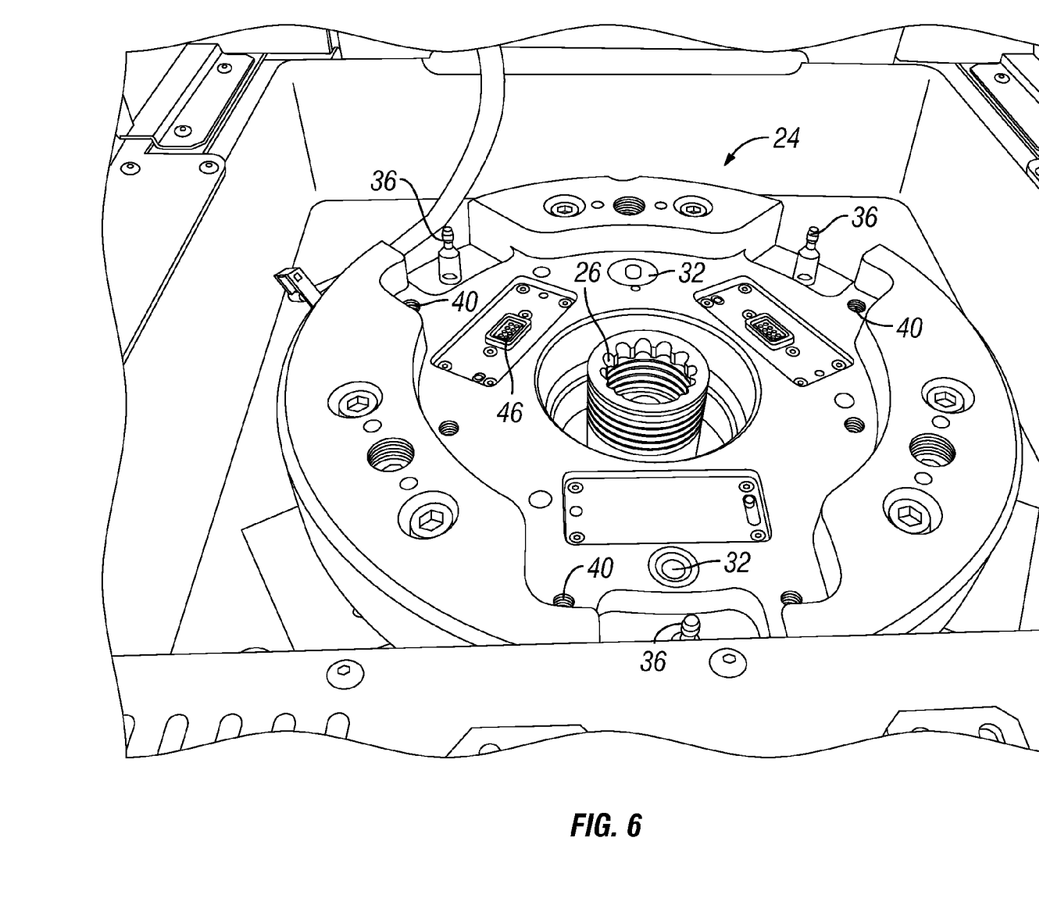
FIG. 6 is a view of the support base for coupling the modular sample stages of invention to the drivetrain contained in the frame of the instrument.

The vertical shaft 28 for coupling the stage with the drivetrain shaft and motor in the base and frame of the tester is a feature common to all modular stages of the invention. Referring back to FIG. 4, the modular stage 14 is of the reciprocating motion kind. It includes a sample holder 42 for receiving a specimen 44 to be tested. The holder 42 is mounted on the stage 14 and is actuated by the shaft 28 to produce a linear reciprocating motion. The length of each stroke is measured as appropriate for a particular test protocol, such as by a Linear Variable Displacement Transducer (LVDT) connected to corresponding software that also controls the frequency of reciprocation. The LVDT device in the sample stage 14 is preferably connected to a microprocessor (not shown) housed in the frame of the tester by means of a blind-mate connector 46 provided for coupling from opposite sides of the stage and base, as seen in FIGS. 5 and 6, respectively. As the stage is positioned over the frame and guided down to cause the shaft 28 to be engaged by the coupling mechanism 26, the two components of the connector 46 are also engaged and communication between the LVTD and the microprocessor is automatically activated.

In what is a particularly important feature of the invention, each modular sample stage is also fitted with a means for its automatic identification, without any operator input. That is, each module contains an identifier that allows the system to immediately recognize the type of stage (reciprocating, rotating, etc.) and to activate only the software pertinent to the operation of that particular type of sample stage. For example, with a reciprocating stage the system would allow an operator to select the stroke length and the frequency of oscillation for a wear test script, or the pattern of tool motion in relation to the sample for a friction measurement, but it would not allow activation of any software corresponding to another sample stage (such as for tests requiring the vertical or horizontal rotation of the sample). This can be achieved by integrating into the drive an IC chip containing an identifying label, such as a 1-Wire® device by Maxim Integrated, or by using an I2C CAN bus or other means known to those skilled in the art. The chips can be embedded in the blind-mate connector 46 that is automatically coupled when the stage is installed on the base 24 of the tester, as seen from FIGS. 5 and 6. Alternatively, such chips can be placed within the connector housing of a more traditional fashion device, such as a DB-9 style connector. An identifier could also consist of a mechanical device triggered by the coupling of the stage to the base of the tester, which in turn would activate the appropriate test protocol. This feature ensures not only that erroneous data are not collected, but, more importantly, also that no dangerous situation is generated by operator error in programming the tester for an incorrect test protocol.

Figure 7:
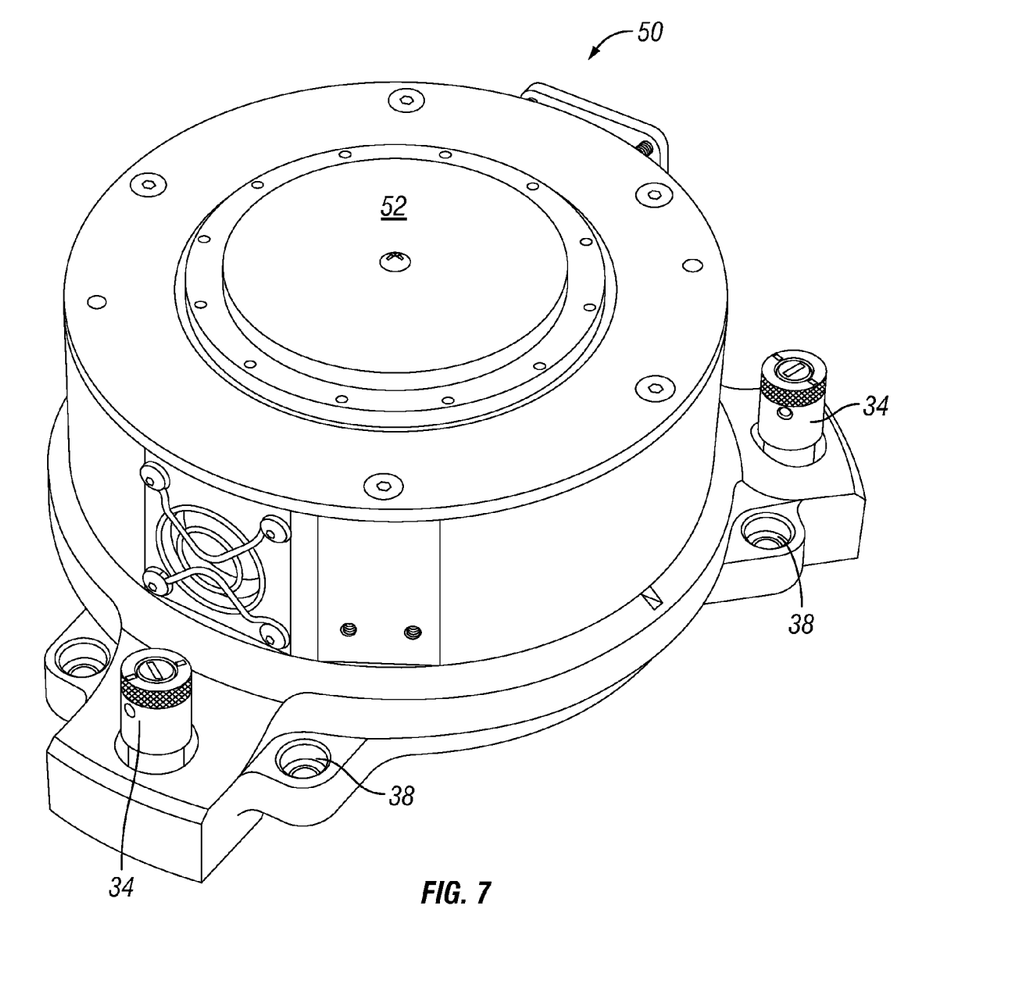
FIG. 7 is a perspective view of a modular sample stage adapted for ball-on-disk, pin-on-disk or disk-on-disk measurements.

FIG. 7 shows in perspective view an alternative modular sample stage 50 dedicated to ball-on-disk, pin-on-disk or disk-on-disk tests. A disk 52 is mounted horizontally on a vertical rotating shaft (not seen) connected to the actuating shaft 28 in the sample stage. The underside of the stage 50 is identical to the one of stage 14 shown in FIG. 5, with the same vertical drive shaft 28 for coupling the stage with the drivetrain shaft and motor in the base and frame of the tester. The same guide pins 30, ball locks 34 and openings 38 are provided to secure the stage within the tester. Blind-mate connectors 46 are similarly used for automatic identification of the stage and for providing appropriate electronic communication with the stage.

Figure 8:
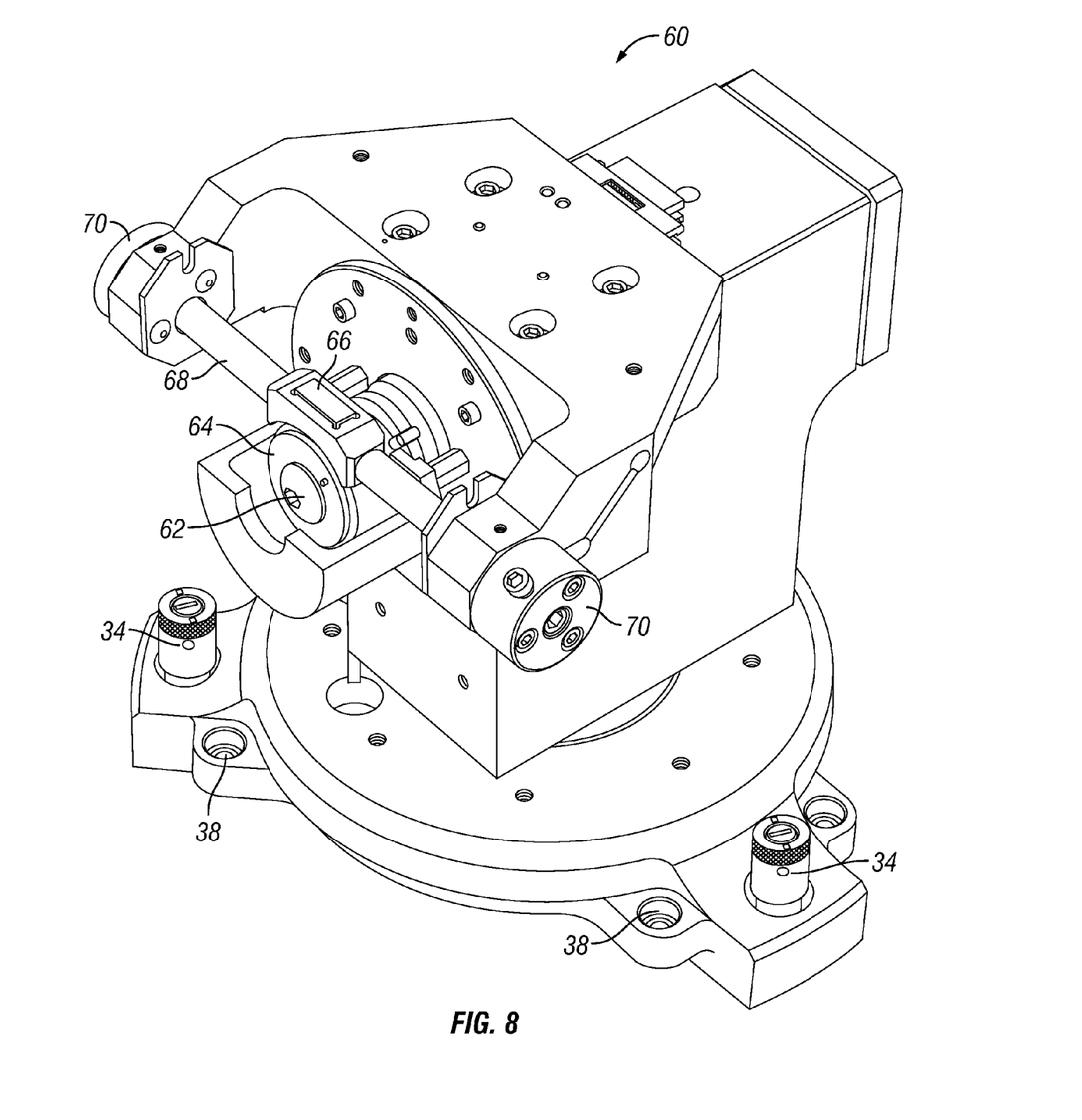
FIG. 8 is a perspective view of a modular sample stage adapted for block-on-ring measurements.

FIG. 8 shows in perspective view another, alternative modular sample stage 60 dedicated to the block-on-ring configuration, where the sample stage includes a drive shaft 62 rotating a ring sample 64 along the shaft's horizontal axis and a block sample 66 forced against it by a support rod 68. Two force sensors 70 measure the forces acting between the two samples. Again, the bottom side of the stage 60 is the same as described with reference to stages 14 and 50.

Figure 9:
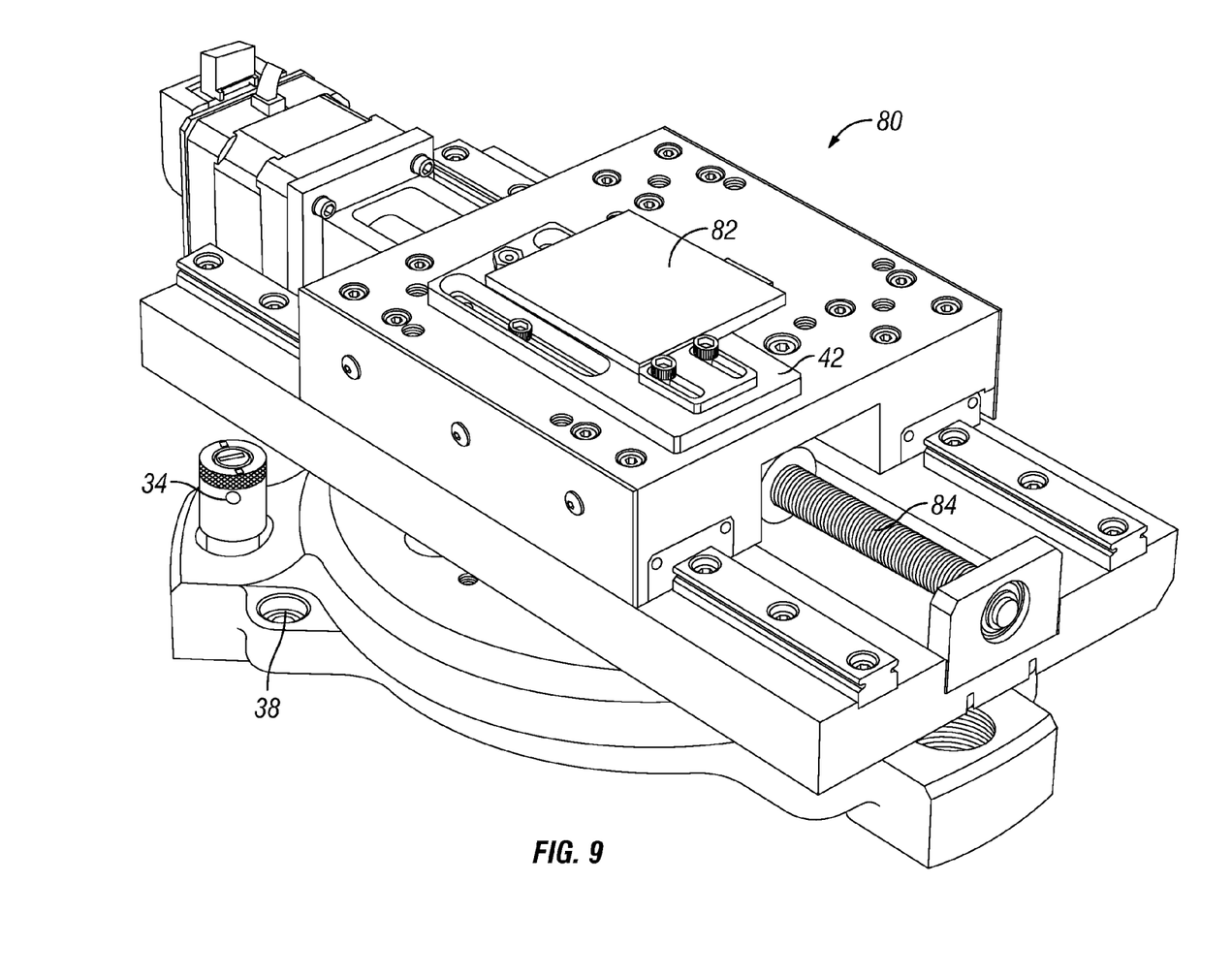
FIG. 9 is a perspective view of a modular sample stage adapted for continuous linear friction and/or scratch tests between upper and lower specimens.

FIG. 9 shows in perspective view yet another, alternative modular sample stage 80 dedicated to tests conducted when the lower specimen 82 is subjected to friction and/or scratch tests involving the continuous linear relative motion between upper and lower specimens. The same features described above for coupling the stage 80 to the base 24 of the tester 10 and for identifying the stage and controlling its operation are present in this module. The rotation of the vertical drive shaft 28 is used to produce in conventional manner the rotation of a horizontal worm screw 84 that in turn causes the sample holder 42 to move along a straight line.

Figure 10:
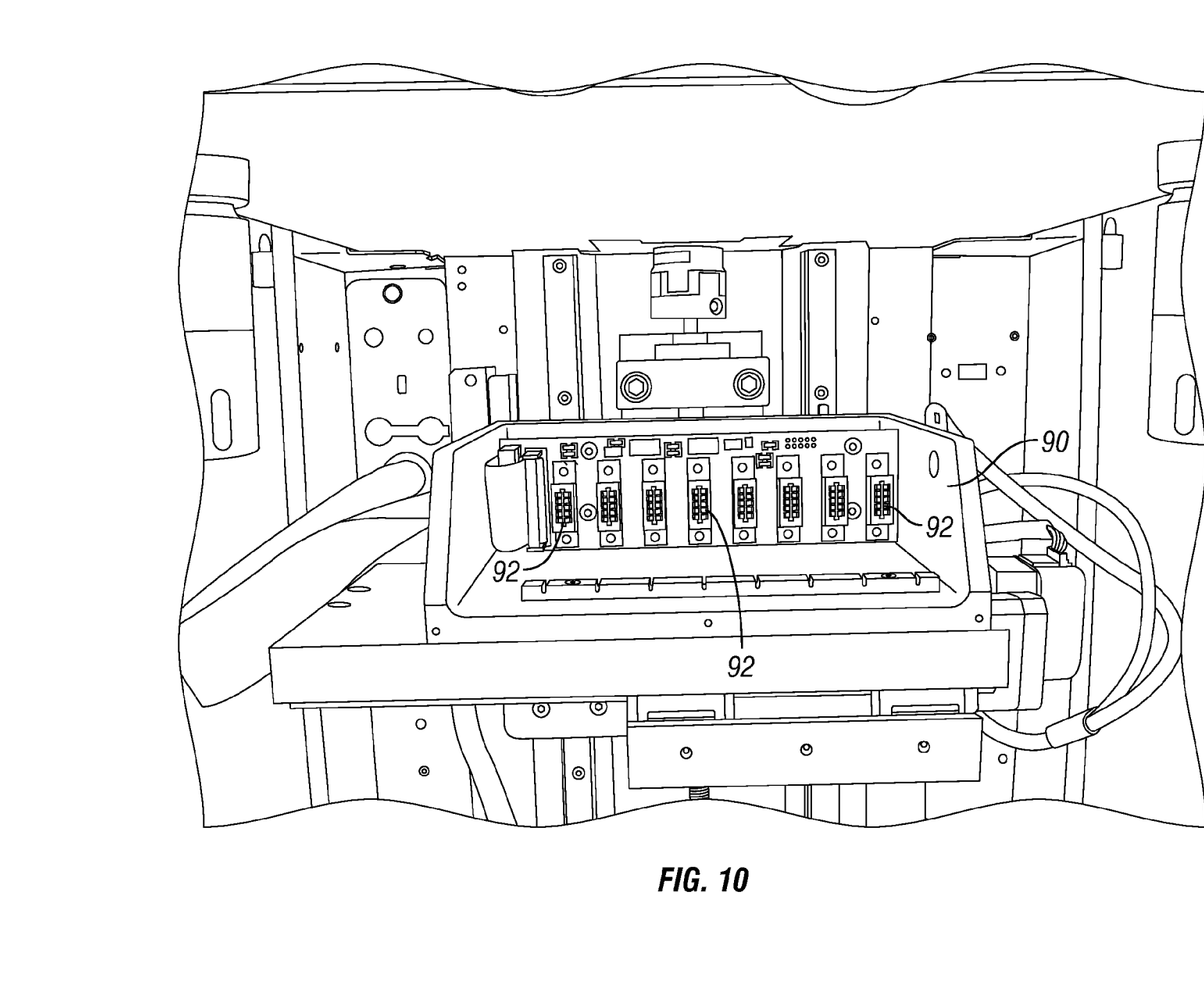
FIG. 10 illustrates a bank of expansion slots provided in the body of the instrument for conducting temperature and humidity control and measurements, as well as voltage and acoustic-emission measurements, with respective expansion cards that contain automatic identifiers for safety and avoidance of operator error.

The tester of the invention further provides sensors for measuring the temperature of the samples and the humidity in the environment containing the samples. As shown in FIG. 10, a bank 90 of slots is provided in the tester for activating respective scripts in software by inserting expansion cards in respective dedicated slots 92 that enable test protocols relevant to temperature and/or humidity measurements, as applicable. Dedicated slots are also available for controlling and measuring voltage applied to the samples and for measuring resistance across the samples, as well as for acoustic-emission measurements on the materials under test. Each such card includes electronic circuitry configured to activate a relevant test protocol and is also labeled with an electronic identification that is automatically recognized by the system's software so as to enable only the scripts relevant to the particular card, thereby avoiding erroneous script implementations.

Thus, the new instrument enables all types of test configurations with a single machine equipped with multiple sample-stage modules, each adapted for a particular type of test protocol. A single drive shaft is fitted with a mechanical quick connect coupler for transferring the torque carried by the drivetrain to each modular sample stage. One such coupler is a bellows coupling such as the MK, BK or BX series of couplings available from R+W® Company, but any coupler that allows for the quick connection of the drive to the drivetrain is suitable for the invention, one that requires no tools being preferred. It is also preferred that the coupler have a bellows or other spring-like flexibility to accommodate misalignments between the shaft of the drivetrain and the drive shaft of the module. It is preferred that the modular stages be held in place by a hold-down mechanism that is tool-less, such as cams, ball-lock assemblies or quick clamps.

It is preferred that any data obtained by calibration of instrument components be saved within the electronics of the component. This allows the component to be plugged into a new piece of equipment and be readily identified with its calibration parameters so the equipment can be used correctly without further calibration. It is also preferred that the data acquisition and motor control electronics be placed within the housing of the unit. This minimizes the electronic requirements of the computer mother board in terms of quantity of slots and slot type. This also minimizes the number of electronic connections between the computer and the test equipment. The test equipment can be designed to be connected with either USB 2.0, USB 3.0 or GigaE or other fast communication protocol. It is understood that a processor programmed for identifying the module currently installed in the tester, for executing a corresponding predetermined set of test operations, and for controlling the various functions of the tester is preferably housed within the frame of the tester 10 but could also be a separate computer connected to the tester when needed.

Thus, a new universal mechanical tester for measuring friction and wear has been described that affords the following improvements:

a quicker change between test configurations;

a single, larger motor positioned within the frame of the instrument rather than in the sample stage, thus leaving more access to the test area;

a larger motor that allows for higher torques than could be achieved previously;

quick mechanical couplers for ease of operation when changing stages;

hardware identification and sensor connections that are automatically enabled when a stage is connected to the system;

automatic hardware identification that allows the software to adapt to the test configuration that is in place showing the user only the relevant information for that particular test configuration; and all of the electronic hardware is placed within the unit, which allows for simplified wiring from the tester to the computer processor. This can be through high-speed means such as USB 2.0, USB 3.0 or GigaE (Ethernet).

Embodiments of the present invention provide a universal apparatus for testing wear and friction characteristics of a material. Such apparatus includes a frame containing a carriage moveable along a vertical plane and a slide moveable along a horizontal plane, a force sensor assembly coupled to the slide, a holder for an upper specimen, the holder being coupled to the force sensor assembly, and a mechanism configured to cause the upper specimen to exert a predetermined force on a lower specimen. The apparatus also includes a plurality of modular sample stages, each of which stages includes a support for the lower specimen and a mechanism for producing a motion of the lower specimen relative to the upper specimen. The motion is rotational around a horizontal axis in one of the stages, rotational around a vertical axis in another of the stages, and linearly reciprocating along a horizontal direction in yet another of the stages. The apparatus additionally includes a base structured to support one of the plurality of modular sample stages, which base incorporates a locking mechanism adapted to couple the stage to the base and a rotational drive adapted for engagement of the mechanism for producing a motion of the lower specimen. The apparatus further includes a motor housed in the frame (which motor is adapted for actuation of the rotational drive), a controller having electronic circuitry programmed to vary the force exerted on the sample, and a processor programmed to execute a predetermined set of test operations.

Related embodiments of the invention additionally provide a universal apparatus for testing wear and friction characteristics of a material that includes a frame containing a carriage moveable along a vertical plane and a slide moveable along a horizontal plane, a force sensor assembly coupled to the slide, a holder for an upper specimen, which holder is coupled to the force sensor assembly, and a mechanism configured to cause the upper specimen to exert a predetermined force on a lower specimen. The apparatus additionally includes a plurality of modular sample stages, each of which stages has a support for the lower specimen and a mechanism for producing a motion of the lower specimen relative to the upper specimen. Such motion is rotational around a horizontal axis in one of the stages, rotational around a vertical axis in another of the stages, and linearly reciprocating along a horizontal direction in yet another of the stages. The apparatus further includes a base structured to alternatively support one of the plurality of modular sample stages, which base has a locking mechanism for coupling the stage to the base and a rotational drive adapted for engagement of the mechanism for producing a motion of the lower specimen. The apparatus additionally includes a motor housed in the frame (which motor is adapted for actuation of the rotational drive), and a controller having electronic circuitry programmed to vary the force exerted on the sample. The apparatus additionally includes a processor programmed to execute a predetermined set of test operations, means for identifying a sample stage coupled to the base and for automatically enabling only a subset of the test operations (which subset corresponds to the sample stage coupled to the base), and means for measuring a temperature of the upper and lower specimens. The apparatus also includes:

an expansion slot and a corresponding expansion card with an enabling electronic identification for activating test protocols relevant only to the means for measuring said temperature;

means for measuring a humidity in an environment containing the upper and lower specimens;

a second expansion slot and a corresponding expansion card with an enabling electronic identification for activating test protocols relevant only to the means for measuring said humidity;

means for controlling and measuring a voltage applied to the upper and lower specimens;

a third expansion slot and a corresponding expansion card with an enabling electronic identification for activating test protocols relevant only to the means for controlling and measuring said voltage;

means for controlling and measuring a resistance across the upper and lower specimens;

a fourth expansion slot and a corresponding expansion card with an enabling electronic identification for activating test protocols relevant only to the means for controlling and measuring said resistance;

means for measuring an acoustic emission of the upper and lower specimens; and a fifth expansion slot and a corresponding expansion card with an enabling electronic identification for activating test protocols relevant to the means for measuring said acoustic emission.

References throughout this specification that may have been made to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same implementation of the invention. It is to be understood that no portion of disclosure, taken on its own and in possible connection with a figure, is intended to provide a complete description of all features of the invention.

In addition, it is to be understood that no single drawing is intended to support a complete description of all features of the invention. In other words, a given drawing is generally descriptive of only some, and generally not all, features of the invention. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

While the invention has been shown and described herein with reference to what are believed to be the most practical embodiments, it is recognized that departures can be made within the scope of the invention and, therefore, the invention is not to be limited to the details disclosed herein but is to be accorded the full scope of equivalent articles.

We claim:

1. A universal apparatus for testing wear and friction characteristics of a material, comprising:
   a frame that includes a carriage moveable along a vertical plane and a slide moveable along a horizontal plane;
   a force sensor assembly coupled to said slide;
   a holder for an upper specimen, said holder being coupled to the force sensor assembly;
   a mechanism for causing said upper specimen to exert a predetermined force on a lower specimen;
   a plurality of modular sample stages, each of said stages including a support for said lower specimen and a mechanism for producing a motion of the lower specimen relative to said upper specimen, said motion being rotational around a horizontal axis in one of said stages, rotational around a vertical axis in another of said stages, and linearly reciprocating along a horizontal direction in yet another of the stages;
   a base for alternatively supporting one of the stages, said base including a locking mechanism for coupling said one of the stages to the base and a rotational drive adapted for engagement of said mechanism for producing a motion of the lower specimen;
   a motor housed in said frame, said motor being adapted for actuation of said rotational drive;
   a controller for varying said force exerted on the sample;
   a processor programmed for executing a predetermined set of test operations; and
   means for identifying said one of the stages coupled to the base and for automatically enabling only a subset of said test operations, said subset corresponding to the one of the stages coupled to the base.

2. The apparatus of claim 1, further including means for measuring a temperature of the upper and lower specimens.

3. The apparatus of claim 2, further including an expansion slot and a corresponding expansion card with electronic circuitry configured to activate test protocols relevant to said means for measuring said temperature.

4. The apparatus of claim 3, wherein said card contains an electronic identification that is automatically recognized by said processor to enable only said test protocols.

5. The apparatus of claim 1, further including means for measuring a humidity in an environment containing said upper and lower specimens.

6. The apparatus of claim 5, further including an expansion slot and a corresponding expansion card with electronic circuitry configured to activate test protocols relevant to said means for measuring said humidity.

7. The apparatus of claim 6, wherein said card contains an electronic identification that is automatically recognized by said processor to enable only said test protocols.

8. The apparatus of claim 1, further including means for controlling and measuring a voltage applied to said upper and lower specimens.

9. The apparatus of claim 8, further including an expansion slot and a corresponding expansion card with electronic circuitry configured to activate test protocols relevant to said means for controlling and measuring said voltage.

10. The apparatus of claim 9, wherein said card contains an electronic identification that is automatically recognized by said processor to enable only said test protocols.

11. The apparatus of claim 1, further including means for controlling and measuring a resistance across said upper and lower specimens.

12. The apparatus of claim 11, further including an expansion slot and a corresponding expansion card with electronic circuitry configured to activate test protocols relevant to said means for controlling and measuring said resistance.

13. The apparatus of claim 12, wherein said card contains an electronic identification that is automatically recognized by said processor to enable only said test protocols.

14. The apparatus of claim 1, further including means for measuring an acoustic emission of said upper and lower specimens.

15. The apparatus of claim 14, further including an expansion slot and a corresponding expansion card with electronic circuitry configured to activate test protocols relevant to said means for measuring said acoustic emission.

16. The apparatus of claim 15, wherein said card contains an electronic identification that is automatically recognized by said processor to enable only said test protocols.

17. A universal apparatus for testing wear and friction characteristics of a material, comprising:
   a frame that includes a carriage moveable along a vertical plane and a slide moveable along a horizontal plane;
   a force sensor assembly coupled to said slide;
   a holder for an upper specimen, said holder being coupled to the force sensor assembly;
   a mechanism for causing said upper specimen to exert a predetermined force on a lower specimen;
   a plurality of modular sample stages, each of said stages including a support for said lower specimen and a mechanism for producing a motion of the lower specimen relative to said upper specimen, said motion being rotational around a horizontal axis in one of said stages, rotational around a vertical axis in another of said stages, and linearly reciprocating along a horizontal direction in yet another of the stages;
   a base for alternatively supporting one of the stages, said base including a locking mechanism for coupling said one of the stages to the base and a rotational drive adapted for engagement of said mechanism for producing a motion of the lower specimen;
   a motor housed in said frame, said motor being adapted for actuation of said rotational drive;
   a controller for varying said force exerted on the sample;

a processor programmed for executing a predetermined set of test operations;

means for identifying a sample stage coupled to the base and for automatically enabling only a subset of said test operations, said subset corresponding to the sample stage coupled to the base;

means for measuring a temperature of the upper and lower specimens;

an expansion slot and a corresponding expansion card with an enabling electronic identification for activating test protocols relevant only to said means for measuring said temperature;

means for measuring a humidity in an environment containing said upper and lower specimens;

a second expansion slot and a corresponding expansion card with an enabling electronic identification for activating test protocols relevant only to said means for measuring said humidity;

means for controlling and measuring a voltage applied to said upper and lower specimens;

a third expansion slot and a corresponding expansion card with an enabling electronic identification for activating test protocols relevant only to said means for controlling and measuring said voltage;

means for controlling and measuring a resistance across said upper and lower specimens;

a fourth expansion slot and a corresponding expansion card with an enabling electronic identification for activating test protocols relevant only to said means for controlling and measuring said resistance;

means for measuring an acoustic emission of said upper and lower specimens; and a fifth expansion slot and a corresponding expansion card with an enabling electronic identification for activating test protocols relevant to said means for measuring said acoustic emission.

* * * * *